United States Patent [19]

Suh et al.

[11] 4,287,203
[45] Sep. 1, 1981

[54] ANTIHYPERTENSIVE 1,4-THIAZEPINE-ONES, 1,4-THIAZONINE-ONES, AND METHOD OF USE THEREOF

[75] Inventors: John T. Suh, Greenwich, Conn.; Bruce E. Williams, Cottage Grove, Minn.; Jerry W. Skiles, Tuckahoe; Bernard Loev, Scarsdale, both of N.Y.

[73] Assignee: USV Pharmaceutical Corporation, Tuckahoe, N.Y.

[21] Appl. No.: 142,945

[22] Filed: Apr. 23, 1980

[51] Int. Cl.³ ............ A61K 31/55; C07D 281/04; C07D 281/18
[52] U.S. Cl. .................. 424/275; 260/239.3 R; 260/239.3 B; 260/239.3 P; 260/239.3 T; 424/246; 424/248.51; 424/258; 424/263; 424/274; 424/273 B; 424/270
[58] Field of Search ............... 260/239.3 R, 239.3 B, 260/239.3 T, 239.3 P; 424/275, 246, 248.51, 258, 263, 274, 273 B, 270

[56] References Cited

PUBLICATIONS

Panizzi, "Gazz. Chim. Ital.", vol. 78, pp. 207-215 and 218.

*Primary Examiner*—Robert T. Bond
*Attorney, Agent, or Firm*—Ernest B. Lipscomb, III

[57] ABSTRACT

Antihypertensive compounds of the structure

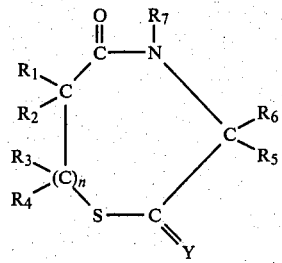

wherein:
n is an integer from 0 to 2 inclusive,
$R_1$, $R_2$, $R_3$, $R_4$, $R_5$, $R_6$, and $R_7$ are independently hydrogen, alkyl having from 1 to 6 carbon atoms, alkenyl having from 2 to 6 carbon atoms, alkynyl having from 2 to 6 carbon atoms, cycloalkyl having from 3 to 16 carbon atoms, phenyl, benzyl, tolyl, naphthyl, phenethyl, indanyl, tetrahydronaphthyl, decanydronaphthyl, pyridyl, quinolyl, pyrrolidyl, pyrrolyl, morpholinyl, thiomorpholinyl, furyl, furfuryl, tetrahydrofurfuryl, benzimidazole, thienyl, imidolyl, or tetrahydroindolyl, and where the $R_1$ to $R_7$ groups are alkyl, said groups carrying a substituent selected from hydroxy, alkoxy, amino, carboxy, or carbalkoxy, the alkyl group in alkoxy and carbalkoxy having from 1 to 6 carbon atoms, or $R_2$ taken together with $R_3$ and the carbons to which they are attached is tetrahydronaphthyl or phenyl, and when phenyl $R_1$ and $R_4$ are absent, or $R_6$ and $R_7$ taken together with the carbon to which $R_6$ is attached and the nitrogen to which $R_7$ is attached form a heterocycle selected from pyrrolidyl, thiazolidine, tetrahydro-isoquinoline, thiomorpholine, or 2,2,5,5-tetramethylthiazolidinie, and
Y is $=O$, $=S$, $=NR_1$, $=NOR_1$ or $=N-NH_2$, $R_1$ being the same as defined above.

21 Claims, No Drawings

ANTIHYPERTENSIVE 1,4-THIAZEPINE-ONES, 1,4-THIAZONINE-ONES, AND METHOD OF USE THEREOF

This invention relates to new chemical compounds possessing valuable pharmaceutical activity. It particularly relates to compounds possessing anti-hypertensive and angiotensin converting enzyme inhibitory activity and having the structure:

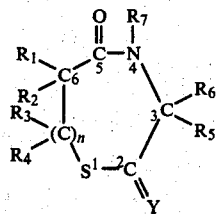

wherein:

n is an integer from 0 to 2 inclusive, $R_1$, $R_2$, $R_3$, $R_4$, $R_5$, $R_6$ and $R_7$ are independently hydrogen, alkyl, alkenyl, alkynyl, cycloalkyl, cycloalkylalkyl, polycycloalkyl, polycycloalkylalkyl, aryl, aralkyl, heteroaryl, heteroarylalkyl, heterocycloalkyl, heterocycloalkyl-alkyl, fused arylcycloalkyl, fused arylcycloalkyl-alkyl, fused heteroaryl-cycloalkyl, fused heteroaryl-cycloalkyl-alkyl, substituted alkyl such as hydroxyalkyl, carboxyalkyl, carbalkoxyalkyl, alkoxyalkyl, alkylthioalkyl, alkylamino-alkyl, or dialkylaminoalkyl, or $R_1$ taken together with $R_2$ and the carbon to which they are attached, $R_3$ taken together with $R_4$ and the carbon to which they are attached, and $R_5$ taken together with $R_6$ and the carbon to which they are attached are cycloalkyl, heterocycloalkyl, heterocycloalkenyl, or cycloalkenyl, or $R_2$ taken together with $R_3$ and the carbons to which they are attached are cycloalkyl, heterocycloalkyl, aryl or heteroaryl, with the proviso that when the rings formed are aryl, or heteroaryl $R_1$ and $R_4$ are absent, and $R_6$ and $R_7$ taken together with with the carbon to which $R_6$ is attached and the nitrogen to which $R_7$ is attached from a heterocyclic ring which may carry substituents such as, alkyl, substituted alkyl, alkenyl, hydroxy, amino, nitro, carboxy, carbalkoxy, aryl, heteroaryl, heterocycloalkyl, and the like; and Y is $=O$, $=S$, $=NR_1—$, $=NOR_1$, or $=N—NH_2$, $R_1$ being the same as defined above.

The alkyl groups per se and in the alkyl moiety in aralkyl, cycloalkyl-alkyl, polycycloalkyl-alkyl, heteroaryl-alkyl and the like, and, in alkoxy, alkylthio, alkanoyl, carbalkoxy, and alkylamino, may be straight chained or branched and contain from 1 to 20 carbons. Preferably, they are lower alkyl groups containing from 1 to 6 carbon atoms. Such groups include methyl, ethyl, propyl, isopropyl, butyl, isobutyl, amyl, iso-amyl, hexyl, and the like.

The alkenyl and alkynyl groups may also be branched or straight-chained and contain from 2 to 20 carbon atoms. Preferably, they contain from 2 to 6 carbon atoms. Such groups include vinyl, ethynyl, propenyl, allyl, isopropenyl, and the like.

The cycloalkyl, polycycloalkyl, aryl, heteroaryl, arylalkyl, fused aryl-cycloalkyl, groups and the like contain from 3 to 16 carbon atoms and may carry substituents such as lower alkyl, alkenyl, alkynyl, hydroxy, thio, amino, alkoxy, alkylthio, alkyl-amino, sulfonyl, sulfon- amido and halo. They include such radicals as cyclopropyl, cyclobutyl, cyclopentyl, cyclohexyl, cycloheptyl, adamantyl, norbornyl, phenyl, tolyl, benzyl, phenethyl, dimethoxyphenyl, hydroxybenzyl, indanyl, naphthyl, tetrahydronaphthyl, decahydronaphthyl, pyridyl, quinolyl, pyrrolidyl, pyrrolyl, morpholinyl, furyl, furfuryl, tetrahydrofurfuryl, benzimidazolyl, thiomorpholinyl, thienyl, imidazolyl, tetrahydroindolyl, and the like.

The alkylene groups may be branched or straight-chained and contain from 1 to B 20 carbon atoms, preferably 1 to 6 carbon atoms. Such groups include methylene, ethylene, propylene, butylene, 1-methyl propylene, 2-ethyl-butylene, and the like.

The alkenylene and alkynylene groups may also be branched or straight-chained and contain from 2 to 16 carbon atoms, preferably 2 to 6 carbon atoms.

Compounds of the present invention may be prepared by heating a compound of the structure:

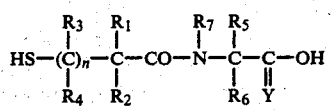

in an inert solvent, preferably a hydrocarbon, in the presence of triphenyl phosphine and 2,2'-dipyridyldisulfide to give

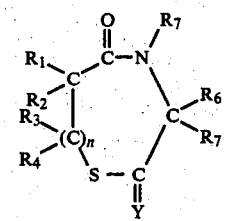

The preparation of some of the starting materials I is described in U.S. patent application Ser. No. 057,175.

Compounds of the present invention may also be prepared by the cyclization of compounds of the structure:

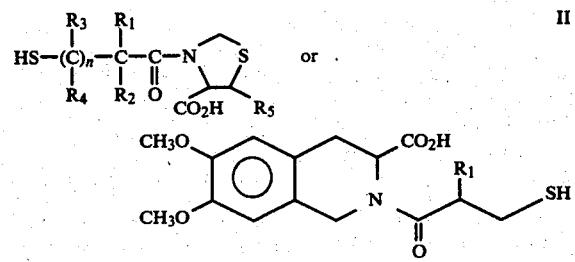

by heating in polyphosphoric acid to give compounds of the structure:

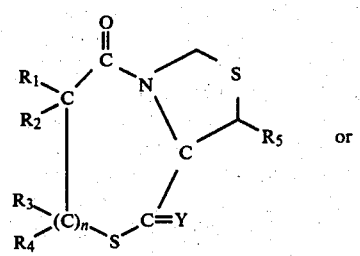

-continued

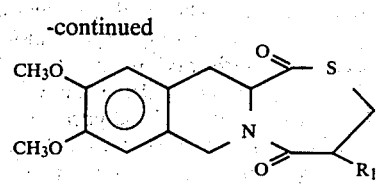

Another suitable synthetic approach is the cyclization of a compound of the structure:

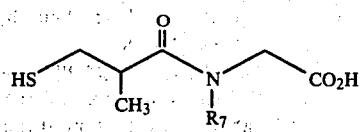

by heating in the presence of triethylamine, methylene chloride and ethyl chloroformate or acyl halides. The cyclization can also be carried out using various activating reagents such as N-ethoxycarbonyl-2-ethoxy-1,2-dihydroquinoline, dicyclohexylcarbodiimide or coupling agents commonly used in the preparation of peptides. These include 1-cyclohexyl-3-(2-morpholinoethyl)carbodrimide metho-p-toluene-sulfonate, 1-(3-dimethylaminopropyl)-3-ethylcarbodiimide hydrochloride, diphenylphosphonyl azide, 2-isobutoxy-1-isobutoxy-carbonyl-1,2-dihydroquinoline, tetraethyl pyrophosphite, trimethylacetyl chloride, 1-hydroxybenzotriazole hydrate, polyphosphoric acid, diethylphosphonyl cyanidate, and the like.

The preparation of dithiolactones and iminothiazepines can be carried out by cyclization reactions of the corresponding mercapto-nitriles and mercapto-iminoethers.

The preparation of suitable intermediates is described in Examples I and XI.

In the above scheme of preparation $R_1$, $R_2$, $R_3$, $R_4$, $R_5$, $R_6$, $R_7$, Y and n are as previously defined.

It is known to those skilled in the art that those compounds of the present invention having asymmetric carbon atoms may exist in racemic or optically active forms. All of these forms are contemplated within the scope of the invention.

The invention will be more fully illustrated in the examples which follow. These examples are given by way of illustration and are not to be considered as limiting.

EXAMPLE I

[N-(2-Mercaptopropanoyl)-N-(cyclopentyl)]glycine

Anhydrous ammonia was bubbled for fifteen minutes through methanol (100 ml) and the resulting ammonia saturated solution was added in one portion to [N-(2-acetylthiopropanoyl)-N-(cyclopentyl)] glycine (5 g, 0.0183 mole) and the system was placed under a slight pressure of nitrogen. The resulting solution was stirred at room temperature for two hours. The solvent was removed in vacuo and the residue was applied to a column of AG-50W-X2 (Bio-Rad Laboratories) cation exchange resin and eluted with methanol. Methanol was evaporated and the residue was dissolved in chloroform. The chloroform was washed once with water and dried over magnesium sulfate. Filtration and evaporation of the solvent afforded the product as a colorless oil (3.8 g, 90%). The product was characterized as its dicyclohexylamine salt, m.p. 163°-164°.

EXAMPLE II

N-(2-Mercaptopropanoyl)-thiazolidine-4-carboxylic acid

N-(2-Acethylthiopropanoyl)-thiazolidine-4-carboxylic acid (3.5 g, 13 mmol) was dissolved in 40 ml of ammonia-saturated methanol and stirred at room temperature for two hours. The solution was concentrated and the residue partitioned between 5% sodium bisulfate solution and ethyl acetate. The organic layer was washed with water and brine, dried over anhydrous magnesium sulfate, filtered and concentrated to give 2.6 g of solid material. This was triturated with acetonitrile to give N-(2-mercaptopropanoly)-thiazolidine-4-carboxylic acid as a colorless solid, m.p. 152°-154°.

EXAMPLE III

4-Cyclopentyl-6,7-dihydro-6-methyl-1,4-thiazepin-2,5-(3H,4H)-dione

A solution of N-cyclopentyl-N-(3-mercapto-2-methylpropanoyl)glycine (2.0 g., 8.1 mmol) in 125 ml of toluene was freed of air by bubbling nitrogen through it. To this solution was then added 2,2'-dipyridyldisulfide (2.7 g., 12.2 mmol) and triphenylphosphine (3.2 g., 12.2 mmol) and the resulting solution was stirred under nitrogen for 5 hours. This solution was then diluted to 250 ml with toluene and added at a rate of 20-25 ml/hr to 2 l of refluxing toluene under nitrogen. The resulting mixture was stirred at reflux for 48 hours and then cooled to room temperature. The solution was washed successively with 0.1 N hydrochloric acid, saturated sodium bicarbonate, water and brine, dried over anhydrous magnesium sulfate, and then filtered and concentrated under vacuum. The resulting solid material was dissolved in 25% ethyl acetate/hexane, filtered to remove the triphenyl phosphine oxide which crystallized, and purified by medium pressure liquid chromatography, eluting with 25% ethyl acetate/hexane, to give 0.8 g. of a pale yellow solid. This solid was recrystallized from 10% ethyl acetate/hexane to give 0.5 g (27%) of 4-cyclopentyl-6,7-dihydro-6-methyl-1,4-thiazapen-2,5-(3H,4H)-dione as a white crystalline solid, mp. 77°-79°.

EXAMPLE IV 4-(exo-2-Bicyclo[2.2.1]heptyl)-6,7-dihydro-6-methyl-1,4-thiazepin-2,5-(3H,4H)-dione A solution of N-(exo-2-bicyclo[2.2.1]heptyl)-N-(3-mercapto-2-methylpropanoyl)glycine (3.5 g, 13 mmol) in 150 ml of toluene was freed of air by bubbling nitrogen through it. To this solution was then added 2,2'-dipyridyldisulfide (4.28 g, 19.5 mmol) and triphenylphosphine (5.1 g, 19.5 mmol) and the resulting solution stirred under nitrogen for 5 hours. This solution was then diluted to 255 ml with toluene and added at a rate of 15 ml/hr to 2.5 l of refluxing toluene. The resulting mixture was stirred at reflux for 48 hours and was then cooled to room temperature. The solution was successively washed with 0.1 N hydrochloric acid, saturated sodium bicarbonate, water and brine, dried over anhydrous magnesium sulfate, and then filtered and concentrated under vacuum. The resulting solid was dissolved in 35% ethyl acetate/hexane, filtered, and purified by medium pressure liquid chromatography, eluting with 35% ethyl acetate/hexane. This gave 1.2 g (36%) of a viscous oil which crystallized with scratching. Half of this material (0.6 g) was dissolved in ethyl acetate, evaporated almost to dryness, and hexane added to give 0.35 g of 4-(exo-2-bicyclo[2.2.1]heptyl)-6,7-dihydro-6-methyl-1,4-thiazapen-2,5-(3H,4H)-dione as a white crystalline solid, m.p. 134°–136°.

EXAMPLE V

6-Methyl-1H,3H-thiazolo[4,3−c][1,4]thiazine-5,8-dione

Polyphosphoric acid (36 g) was added to N-(2-mercaptopropanoyl) thiazolidine-4-carboxylic acid (1.5 g, 6.78 mmol) and the mixture stirred at 50° for a period of 4 hours. The reaction mixture was then dissolved in water and extracted with ethyl acetate. The organic layer was washed with water and brine, dried over magnesium sulfate, filtered and concentrated to give 0.7 g of 6-methyl-1H,3H-thiazolo[4,3−c][1,4]thiazine-5,8-dione as a pale yellow oil.

EXAMPLE VII (4R-trans)-Hexahydro-4-methyl-1H,5H-pyrrolo[2,1−c][1,4]thiazepine-1,5-dione A solution of (D-3-mercapto-2-methylpropanoyl)-L-proline (S,S) (817 mg, 3.76 mmol) in 30 ml of methylene chloride was cooled to 0° and triethylamine (380 mg, 3.76 mmol) added. Then a solution of ethyl chloroformate (408 mg, 3.76 mmol) in 9 ml of methylene chloride was added rapidly dropwise. The reaction mixture was then stirred for 3.5 hours, warming slowly to room temperature. The mixture was washed with water and brine, dried with anhydrous magnesium sulfate, filtered, and concentrated to give a white solid. This was triturated with 95% hexane/ether and filtered to give 451 mg (60%) of crystalline (4R-trans)-hexahydro-4-methyl-1H,5H-pyrrolo[2,1−c][1,4]thiazepine-1,5-dione, m.p. 98°–101°, $[\alpha]_D = 119.0°$.

EXAMPLE VIII

Hexahydro-7-methyl-1H,3H-thiazolo[4,3−c][1,4]-thiazepine-1,5-dione

A solution of N-(3-mercapto-2-methylpropanoyl)-thiazolidine-4-carboxylic acid (7.1 g, 30.2 mmol) in 250 ml of methylene chloride was cooled to 0° and triethylamine (5.78 g, 30.2 mmol) was added. Then ethyl chloroformate (2.55 g, 30.2 mmol) in 50 ml of methylene chloride was added dropwise over 75 minutes. The solution was then stirred for 3.5 hours while the bath returned to room temperature. The solution was washed with water, dried over anhydrous sodium sulfate, filtered, and concnetrated to give 6.5 g of crude product. This material was purified by HPLC to give 0.9 g of solid hexahydro-7-methyl-1H,3H-thiazolo[4,3−c][1,4]thiazepine-1,5-dione, mp 70°–100°, $[\alpha]_D = -82.3°$.

EXAMPLE IX

Hexahydro-4-methyl-6,7,12,13-tetrahydroisoquinoline-[3,2−c][1,4]thiazepine-1,5-dione A solution of [N-(3-mercapto-2-methylpropanoyl-L-(1,2,3,4-tetrahydroisoquinoline)]1-3-carboxylic acid (2.5 g, 0.00896 moles) in chloroform (100 ml) was chilled in an ice bath and triethylamine (0.91 g, 0.009 mole) was added. Ethyl chloroformate (0.97 g, 0.009 mole) in chloroform (40 ml) was added dropwise over 10 minutes. The resulting solution was then stirred for two and a half hours at room temperature. The chloroform was washed with water, saturated sodium chloride, and dried over magnesium sulfate. Filtration and evaporation of the solvent afforded the crude product as a yellow oil which was chromatographed on silica-gel (CHCl₃) to give the desired 1,5-dione as colorless crystals (1.1 g, 43%), crystallized from ether-hexane, m.p. 142°.

EXAMPLE IX

6-Methyl[1,4]thiazine-2,5-dione

A solution of N-(2-mercaptopropanoyl) glycine (5 g, 0.031 mole) in methylene chloride (250 ml) was chilled in an ice bath and triethylamine (3.1 g, 0.031 mole) was added. Ethyl chloroformate (3.4 g, 0.031 mole) in methylene chloride (25 ml) was added dropwise over 15 minutes. The resulting solution was then stirred for two and a half hours at room temperature. The methylene chloride was washed with water, saturated aqueous sodium chloride, and dried over magnesium sulfate. Filtration and evaporation of the solvent afforded the crude product as a yellow oil which was chromatographed on silica-gel (CHCl₃) to yield colorless crystals of 6-methyl[1,4]thiazine-2,5-dione (1.5 g, 30%) after crystallization from ether-hexane, m.p. 81°–83°.

EXAMPLE XI

N-Cyclopentyl-6-methyl[1,4]thiazine-2,5-dione

A solution of [N-(2-mercaptopropanoyl)-N-(cyclopentyl)] glycine (3.0 g, 0.0139 mole) in methylene chloride (150 ml) was chilled in an ice bath and triethylamine (1.4 g, 0.0139 mole) was added. Ethyl chloroformate (1.5 g, 0.0139 mole) in methylene chloride (20 ml) was added dropwise over 10 minutes. The resulting solution was stirred for two and a half hours at room temperature. The methylene chloride was washed with water, saturated sodium chloride, and dried over magnesium sulfate. Filtration and evaporation of the solvent afforded the crude product as a pale yellow oil which was chromatographed on silica-gel (CHCl₃) to afford after crystallization (ether-hexane)N-cyclopentyl-6-methyl[1,4]thiazine-2,5-dione as colorless crystals (0.9 g, 25.7%), m.p. 66°–68°.

Following the procedures described in the above examples, the following additional compounds were prepared:

4-Cyclopentyl-6,7-dihydro-6-methyl-1,4-oxazapine-2,5-(3H,4H)-dione,

Hexahydro-4-cyclopentyl-6-methyl-1,4-diazepine-2,5-dione,

4-Cyclopentyl-6-methyl-benzo[1,2-f][1,4]thiazapine-2,5-(3H,4H) dione,

4-Cyclohexyl-6,7-dihydro-6-methyl-1,4-diazapine-2-methylimino-5-(3H,4H)-one,

Tetrahydro-4-ethyl-piperidino[2,1-c][1,4]thiazapine-1-thiooxy-5-one, 4-(4-pyridyl)-6,7-dihydro-6-methyl-1,4-thiazapine-2,5-(3H,4H)-dione, 4-cyclopentyl-6-ethylidene-1,4-thiazapine-2,5-(3H,4H,7H)-dione, 4-(4-methylphenyl)-6-methyl-benzo[2,3-f][1,4]-thiazapine-2,5-(3H,4H)-dione, 1,1,3,3,6-pentamethyl-1H,3H-thiazolo[4,3-C][1,4]thiazine-5,8-dione, Hexahydro-4,10-dimethyl-1H,5H-pyrrolo[2,1-C][1,4]thiazepine-1,5-dione, Hexahydro-4-methyl-6,7-dihydroisoquinolino[3,4−c][1,4]thiazepine-1,5-dione, Hexahydro-4-methyl-10,11-dimethyl-6,7,8,13-tetrahydroisoquinolino[1,2-C][1,4]thiazepine-1,5-dione, N-Cyclopentyl-3,3,6,6-tetramethyl[1,4]thiazine-2,5-dione, Hexahydro-4-methyl-6,8,12,13-tetrahydro-1,7-Naphthylidino[6,7-C][1,4]thiazepine-1,5-dione, 3-Methyl-5,6,11,12-tetrahydroisoquinoline[3,2—C][1,4]thiazine-1,4-dione, 3-Methyl-1H,4H-pyrrolo[2,1-C][1,4]thiazine-1,4-dione, 4-Cyclopentyl-6,7dihydro-6-methyl-2-imino-1,4-thiazepin-5-(3H,4H)-one, 4-Methyl-7-phenyl-6,7,13,14-tetrahydro-carbonylβ[3,2—C][1,4]thiazepine-1,5-dione, 4-Cyclopentyl-tetrahydro-benzo[1,4]thiazepine-2,5-dione, Hexahydro-4-methyl-azabicyclo[2.2.2]octyl[2,1—C][1,4]thiazepine-1,5-dione, 3-Methyl-5,11-dihydrobenzothiazolo[3,2—C][1,4]thiazine-1,4-dione, 2-Methyl-2,3,6,7,7a,8-hexahydro-1,3-thiazolo[3,4-d][1,4-thiazin]-3,8-dione.

The compounds of the present invention have demonstrated potent activity (of the order $I_{50}$ of 0.0075 to 0.05 micromols) in inhibiting the angiotensin converting enzyme (ACEI activity) when tested by the method described in Science 196, 441–4 (1977). As such, these compounds would be very useful in the treatment of hypertension. Administration of the compounds of hypertensive rats at dosages of about 100 mg/kg i.p. decreases the blood pressure by about 25 to 35% for periods of about 10–13 hours. The compounds may be administered orally or parenterally in the treatment of hypertension and it will be within the skill of the practitioner to determine the exact amount to be administered and the mode of administration.

We claim:

1. A compound of formula

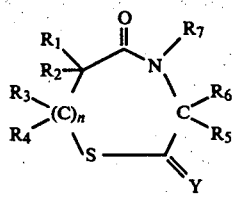

wherein:

n is an integer from 0 to 2 inclusive, $R_1$, $R_2$, $R_3$, $R_4$, $R_5$, $R_6$ and $R_7$ are independently hydrogen, alkyl having from 1 to 6 carbon atoms, alkenyl having from 2 to 6 carbon atoms, alkynyl having from 3 to 6 carbon atoms, cycloalkyl having from 3 to 16 carbon atoms, phenyl, benzyl, tolyl, phenethyl, naphthyl, tetrahydronaphthyl, indanyl, decahydronaphthyl, or substituted alkyl wherein the alkyl group has 1 to 6 carbon atoms and the substituent is selected from the group consisting of hydroxy, amino, carboxy, alkoxy and carbalkoxy, the alkyl group in alkoxy or carbalkoxy having 1 to 6 carbon atoms, and Y is $=O$, $=S$, $=NR_1$, $=NOR_1$ or $=N-NH_2$, $R_1$ being the same as defined above.

2. A compound according to claim 1 wherein $R_1$ is methyl.

3. A compound according to claim 2 wherein $R_2$ is hydrogen.

4. A compound according to claim 3 wherein Y is $=O$.

5. A compound according to claim 4 wherein $R_5$ is hydrogen or methyl.

6. A compound according to claim 5 wherein n is 0.

7. A compound according to claim 5 wherein n is 1.

8. A compound according to claim 7 wherein $R_3$ and $R_4$ are hydrogen.

9. A compound according to claim 6 wherein $R_6$ is hydrogen or methyl.

10. A compound according to claim 7 wherein $R_6$ is hydrogen or methyl.

11. A compound according to claim 9 wherein $R_7$ is cycloalkyl.

12. A compound according to claim 11 wherein $R_7$ is cyclopentyl.

13. A compound acccording to claim 10 wherein $R_7$ is cycloalkyl.

14. A compound according to claim 13 wherein $R_7$ is cyclopentyl, norbornyl or indanyl.

15. A compound according to claim 14 wherein $R_7$ is cyclopentyl.

16. A compound according to claim 15 wherein $R_3$, $R_4$, $R_5$ and $R_6$ are hydrogen.

17. A compound according to claim 9 wherein $R_5$ is hydrogen and $R_7$ is carbo-t-butoxymethyl or carboxymethyl.

18. A compound according to claim 12 wherein $R_5$ is hydrogen.

19. A compound according to claim 9 wherein $R_5$ is hydrogen, and $R_7$ is p-tolyl.

20. A compound according to claim 10 wherein $R_5$ is hydrogen, and $R_7$ is p-tolyl.

21. A method for reducing blood pressure in mammals having hypertension which comprises administering an anti-hypertensivelly effective amount of a compound of claim 1.

* * * * *